(12) United States Patent
Sheth et al.

(10) Patent No.: US 10,729,548 B2
(45) Date of Patent: Aug. 4, 2020

(54) BIOACTIVE SOFT TISSUE IMPLANT AND METHODS OF MANUFACTURE AND USE THEREOF

(71) Applicant: Howmedica Osteonics Corp., Mahwah, NJ (US)

(72) Inventors: Sonny Sheth, Berwyn, PA (US); David Arazawa, Hummelstown, PA (US); J. Brook Burley, Mountain View, CA (US); Sarah Elizabeth Smith, West Chester, PA (US); Matthew B. Havener, Conshohocken, PA (US); James San Antonio, Media, PA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 15/584,620

(22) Filed: May 2, 2017

(65) Prior Publication Data
US 2017/0312080 A1 Nov. 2, 2017

Related U.S. Application Data

(60) Provisional application No. 62/330,584, filed on May 2, 2016.

(51) Int. Cl.
*A61F 2/28* (2006.01)
*A61L 31/16* (2006.01)
(Continued)

(52) U.S. Cl.
CPC ............ *A61F 2/28* (2013.01); *A61F 2/30767* (2013.01); *A61F 2/4601* (2013.01); *A61L 27/02* (2013.01);
(Continued)

(58) Field of Classification Search
None
See application file for complete search history.

(56) References Cited

U.S. PATENT DOCUMENTS

| 4,655,777 A | 4/1987 | Dunn et al. |
| 5,711,960 A | 1/1998 | Shikinami |

(Continued)

FOREIGN PATENT DOCUMENTS

| EP | 1604649 A1 | 12/2005 |
| WO | 01038428 A1 | 5/2001 |

(Continued)

OTHER PUBLICATIONS

A. Oryan et al., Bone regenerative medicine: classic options, novel strategies, and future directions, J. Orthop. Surg. Res. Mar. 17, 2014; 9(1):18.

(Continued)

*Primary Examiner* — David H Willse
*Assistant Examiner* — Javier G Blanco
(74) *Attorney, Agent, or Firm* — Lerner, David, Littenberg, Krumholz & Mentlik, LLP

(57) ABSTRACT

A bioactive filamentary structure includes a sheath coated with a mixture of synthetic bone graft particles and a polymer solution forming a scaffold structure. In forming such a structure, synthetic bone graft particles and a polymer solution are applied around a filamentary structure. A polymer is precipitated from the polymer solution such that the synthetic bone graft particles and the polymer coat the filamentary structure and the polymer is adhered to the synthetic bone graft particles to retain the graft particles.

26 Claims, 7 Drawing Sheets

(51) Int. Cl.
  *A61L 31/12* (2006.01)
  *A61L 31/00* (2006.01)
  *A61F 2/30* (2006.01)
  *A61F 2/46* (2006.01)
  *A61L 27/02* (2006.01)
  *A61L 27/36* (2006.01)
  *A61L 27/40* (2006.01)
  *A61L 27/26* (2006.01)

(52) U.S. Cl.
  CPC .......... *A61L 27/025* (2013.01); *A61L 27/365* (2013.01); *A61L 27/3645* (2013.01); *A61L 27/40* (2013.01); *A61L 31/005* (2013.01); *A61L 31/127* (2013.01); *A61L 31/16* (2013.01); *A61F 2/30965* (2013.01); *A61F 2002/2835* (2013.01); *A61F 2002/3006* (2013.01); *A61F 2002/30062* (2013.01); *A61F 2002/3093* (2013.01); *A61L 27/26* (2013.01); *A61L 2420/02* (2013.01); *A61L 2420/06* (2013.01); *C12N 2533/18* (2013.01)

(56) References Cited

U.S. PATENT DOCUMENTS

| | | | |
|---|---|---|---|
| 5,876,446 A * | 3/1999 | Agrawal | A61F 2/30767 623/23.61 |
| 5,914,356 A | 6/1999 | Erbe | |
| 5,939,039 A | 8/1999 | Sapieszko et al. | |
| 5,989,463 A | 11/1999 | Tracy et al. | |
| 6,165,486 A | 12/2000 | Marra et al. | |
| 6,379,962 B1 | 4/2002 | Holy et al. | |
| 6,383,519 B1 | 5/2002 | Sapieszko et al. | |
| 6,482,444 B1 | 11/2002 | Bellantone et al. | |
| 6,517,542 B1 | 2/2003 | Papay et al. | |
| 6,521,246 B2 | 2/2003 | Sapieszko et al. | |
| 6,599,323 B2 | 7/2003 | Melican et al. | |
| 6,709,744 B1 | 3/2004 | Day et al. | |
| 6,730,252 B1 | 5/2004 | Teoh et al. | |
| 6,756,060 B1 | 6/2004 | Greenspan et al. | |
| 6,852,330 B2 | 2/2005 | Bowman et al. | |
| 6,884,428 B2 | 4/2005 | Binette et al. | |
| 6,974,862 B2 | 12/2005 | Ringeisen et al. | |
| 6,991,803 B2 | 1/2006 | Sapieszko et al. | |
| 7,056,409 B2 | 6/2006 | Dubrow | |
| 7,074,294 B2 | 7/2006 | Dubrow | |
| 7,074,894 B2 | 7/2006 | Walker et al. | |
| 7,189,263 B2 | 3/2007 | Erbe et al. | |
| 7,214,765 B2 | 5/2007 | Ringeisen et al. | |
| 7,235,290 B2 | 6/2007 | Vallittu et al. | |
| 7,344,617 B2 | 3/2008 | Dubrow | |
| 7,368,124 B2 | 5/2008 | Chun et al. | |
| 7,494,950 B2 | 2/2009 | Armitage et al. | |
| 7,519,017 B2 | 4/2009 | Yi | |
| 7,531,004 B2 | 5/2009 | Bagga et al. | |
| 7,534,451 B2 | 5/2009 | Erbe et al. | |
| 7,608,098 B1 | 10/2009 | Stone et al. | |
| 7,651,769 B2 | 1/2010 | Dubrow | |
| 7,651,869 B2 | 1/2010 | Saaski et al. | |
| 7,723,395 B2 | 5/2010 | Ringeisen et al. | |
| 7,842,737 B2 | 11/2010 | Wang et al. | |
| 7,910,690 B2 | 3/2011 | Ringeisen et al. | |
| 7,955,381 B1 | 6/2011 | Wang et al. | |
| 7,959,940 B2 | 6/2011 | Gale et al. | |
| 7,964,206 B2 | 6/2011 | Suokas et al. | |
| 7,972,616 B2 | 7/2011 | Dubrow et al. | |
| 7,985,475 B2 | 7/2011 | Dubrow | |
| 8,071,007 B1 | 12/2011 | Teoh et al. | |
| 8,114,161 B2 | 2/2012 | Evans et al. | |
| 8,119,705 B2 | 2/2012 | Wang et al. | |
| 8,128,626 B2 | 3/2012 | Justin | |
| 8,133,500 B2 | 3/2012 | Ringeisen et al. | |
| 8,167,881 B2 | 5/2012 | Justin | |
| 8,188,229 B2 | 5/2012 | Ringeisen et al. | |
| 8,192,665 B2 | 6/2012 | Huang et al. | |
| 8,197,837 B2 | 6/2012 | Jamiolkowski et al. | |
| 8,287,915 B2 | 10/2012 | Clineff et al. | |
| 8,309,114 B2 | 11/2012 | Gale et al. | |
| 8,343,530 B2 | 1/2013 | Wang et al. | |
| 8,377,356 B2 | 2/2013 | Huang et al. | |
| 8,389,588 B2 | 3/2013 | Ringeisen et al. | |
| 8,394,139 B2 | 3/2013 | Roeder et al. | |
| 8,394,488 B2 | 3/2013 | Dave et al. | |
| 8,425,591 B1 | 4/2013 | Wang et al. | |
| 8,439,947 B2 | 5/2013 | Howard et al. | |
| 8,445,554 B2 | 5/2013 | Ringeisen et al. | |
| 8,475,531 B1 * | 7/2013 | Maxson | A61F 2/30756 623/14.12 |
| 8,512,735 B2 | 8/2013 | Gale et al. | |
| 8,563,024 B2 | 10/2013 | Bratt et al. | |
| 8,613,877 B2 | 12/2013 | Huang et al. | |
| 8,633,299 B2 | 1/2014 | Ringeisen et al. | |
| 8,691,259 B2 | 4/2014 | Bowman et al. | |
| 8,696,739 B2 | 4/2014 | Dierking et al. | |
| 8,702,808 B2 | 4/2014 | Teoh et al. | |
| 8,753,391 B2 | 6/2014 | Lu et al. | |
| 8,778,378 B2 | 7/2014 | Clineff et al. | |
| 8,821,494 B2 | 9/2014 | Pilgeram | |
| 8,828,419 B2 | 9/2014 | Dave et al. | |
| 8,834,468 B2 | 9/2014 | Justin | |
| 8,858,617 B2 | 10/2014 | Roeder et al. | |
| 8,864,843 B2 | 10/2014 | Lu et al. | |
| 8,870,945 B2 | 10/2014 | Dave et al. | |
| 8,876,864 B2 | 11/2014 | Spedden et al. | |
| 8,895,045 B2 | 11/2014 | Jamiolkowski et al. | |
| 8,956,637 B2 | 2/2015 | Dubrow et al. | |
| 8,999,369 B2 | 4/2015 | Gale et al. | |
| 9,144,482 B2 | 9/2015 | Sayet | |
| 9,144,487 B2 | 9/2015 | Wang et al. | |
| 9,199,004 B2 | 12/2015 | Wang et al. | |
| 9,211,184 B2 | 12/2015 | Stone et al. | |
| 9,216,076 B2 | 12/2015 | Mitra et al. | |
| 9,220,598 B2 | 12/2015 | Betz et al. | |
| 9,333,082 B2 | 5/2016 | Wei et al. | |
| 9,445,803 B2 | 9/2016 | Marchand et al. | |
| 9,913,710 B2 | 3/2018 | Perriello et al. | |
| 9,974,534 B2 | 5/2018 | Troxel et al. | |
| 2002/0055759 A1 * | 5/2002 | Shibuya | A61B 17/06166 606/231 |
| 2002/0127265 A1 | 9/2002 | Bowman et al. | |
| 2002/0183858 A1 | 12/2002 | Contiliano et al. | |
| 2003/0003127 A1 | 1/2003 | Brown et al. | |
| 2004/0062753 A1 | 4/2004 | Rezania et al. | |
| 2004/0078090 A1 | 4/2004 | Binette et al. | |
| 2004/0185085 A1 | 9/2004 | Ochi et al. | |
| 2004/0197367 A1 | 10/2004 | Rezania et al. | |
| 2004/0197375 A1 | 10/2004 | Rezania et al. | |
| 2005/0161857 A1 | 7/2005 | Coombes et al. | |
| 2005/0208094 A1 | 9/2005 | Armitage et al. | |
| 2006/0178748 A1 * | 8/2006 | Dinger, III | A61B 17/1615 623/18.11 |
| 2006/0195179 A1 | 8/2006 | Sun et al. | |
| 2006/0233887 A1 | 10/2006 | Day | |
| 2007/0093912 A1 | 4/2007 | Borden | |
| 2007/0218424 A1 | 9/2007 | Vuorisalo et al. | |
| 2007/0255422 A1 | 11/2007 | Wei et al. | |
| 2008/0051881 A1 | 2/2008 | Feng et al. | |
| 2008/0081063 A1 | 4/2008 | Wang et al. | |
| 2008/0082177 A1 | 4/2008 | Yang et al. | |
| 2008/0085292 A1 | 4/2008 | Rezania et al. | |
| 2009/0028921 A1 | 1/2009 | Arinzeh | |
| 2009/0075382 A1 | 3/2009 | Sachlos | |
| 2009/0163936 A1 | 6/2009 | Yang et al. | |
| 2009/0198167 A1 | 8/2009 | Ambrosio | |
| 2009/0220566 A1 | 9/2009 | Barralet et al. | |
| 2009/0312792 A1 | 12/2009 | Fallin et al. | |
| 2009/0318962 A1 | 12/2009 | Spedden et al. | |
| 2010/0047309 A1 | 2/2010 | Lu et al. | |
| 2010/0113642 A1 | 5/2010 | Leskela et al. | |
| 2010/0234947 A1 | 9/2010 | Ben Rubi et al. | |
| 2010/0234966 A1 | 9/2010 | Lo | |
| 2010/0310623 A1 | 12/2010 | Laurencin et al. | |
| 2011/0022085 A1 | 1/2011 | Murphy et al. | |

(56) References Cited

U.S. PATENT DOCUMENTS

| | | | |
|---|---|---|---|
| 2011/0118827 A1 | 5/2011 | Wu | |
| 2011/0125189 A1 | 5/2011 | Stoll, Jr. et al. | |
| 2012/0029561 A1* | 2/2012 | Olson | A61B 17/06166 606/228 |
| 2012/0040015 A1 | 2/2012 | Lehtonen et al. | |
| 2012/0071566 A1 | 3/2012 | Kelly et al. | |
| 2012/0101593 A1 | 4/2012 | D'Agostino et al. | |
| 2013/0090686 A1 | 4/2013 | Stopek et al. | |
| 2013/0131722 A1 | 5/2013 | Marchand et al. | |
| 2013/0202670 A1 | 8/2013 | Darmoc et al. | |
| 2013/0238027 A1 | 9/2013 | Zhang et al. | |
| 2013/0282140 A1 | 10/2013 | Ringeisen et al. | |
| 2014/0039552 A1 | 2/2014 | Pilgeram | |
| 2014/0142686 A1 | 5/2014 | Wu | |
| 2014/0200667 A1* | 7/2014 | Carter | A61L 27/56 623/13.18 |
| 2014/0207138 A1 | 7/2014 | Justin | |
| 2014/0287014 A1 | 9/2014 | Ringeisen et al. | |
| 2014/0350680 A1 | 11/2014 | Le et al. | |
| 2015/0018878 A1 | 1/2015 | Rizk et al. | |
| 2015/0051643 A1 | 2/2015 | Spedden et al. | |
| 2015/0100121 A1 | 4/2015 | Lu et al. | |
| 2015/0230918 A1 | 8/2015 | Detamore et al. | |
| 2016/0000974 A1 | 1/2016 | Arinzeh et al. | |
| 2016/0144066 A1 | 5/2016 | Long et al. | |
| 2017/0043052 A1 | 2/2017 | San Antonio et al. | |

FOREIGN PATENT DOCUMENTS

| | | |
|---|---|---|
| WO | 0240069 A2 | 5/2002 |
| WO | 20080134807 A1 | 11/2008 |

OTHER PUBLICATIONS

A.G.A. Coombes et al, Precipitation Casting of Polycaprolactone for Applications in Tissue Engineering and Drug Delivery, Biomaterials 2004, 25, 315-325.

A.G.A. Coombes et al, Precipitation Casting of Polycaprolactone for Applications in Tissue Engineering and Drug Delivery, Biomaterials, Jan. 1, 2004, vol. 25, No. 2, 315-325.

Adams et at., J. of Knee Surgery, Tissue Engineering for Meniscus Repair, vol. 18(1), 2005, pp. 25-30.

Amoczky et aL, J. of Bone and Joint Surgery, Meniscal Repair Using an Exogenous Fibrin Clot, vol. 70A(8), 1988, pp. 1200-1217.

Aparecida et al., "Biomimetic apatite formation on Ultra-High Molecular Weight Polyethylene (UHMWPE) using modified biomimetic solution", J. Mater Sci: Mater Med (200(0 20:1215-1222.

Australian Examination Report for Application No. 2007284135 dated Nov. 1, 2013.

Australian Examination Report for Application No. 2007284135 dated Sep. 9, 2013.

B. Azimi, et al. Journal of Engineering Fibers and Fabrics vol. 9, Issue 3 (2014) p. 74-90.

Boccaccini e al., "Composite surgical sutures with bioactive glass coating", Journal of Biomedical Materials REsearch Part B: Applied Biomaterials, vol. 67B, Issue 1, pp. 618-626, Oct. 15, 2003.

Bordes, C., et al., 2010, International J. Pharmaceutics, 383, 236-243.

Bretcanu et al., "Bioactivity of degradable polymer sutures coated with bioactive glass", Journal of Materials Science: Materials in Medicine 15 (2004) 893-899.

European Search Report for Application No. 16183881.8 dated Dec. 19, 2016.

European Search Report for Application No. EP07800009.8 dated Feb. 12, 2015.

Fox et al, J. of Arthroscopic and Related Surgery, Treytination of Incomplegte Meniscal Tears,9(4), 1993, pp. 451-455.

Gosain, A. Bioactive Glass for Bone Replacement in Craniomaxillofacial Reconstruction, Plastic and Reconstructive Surgery (2004) vol. 114, No. 2, pp. 590-593.

K. Makornkaewkeyoon, Polycaprolactone Matrices generated in aqueous media: natural polymers immobilization and stress relaxation behavior. Masters thesis, Oklahoma State University, 2007, 74 pages.

M.A. Woodruff and D.W. Hutmacher, The return of a forgotten polymer: polycaprolactone in the 21st century, Progress in Polymer Science, p. 1-102, Elsevier Press, 2010.

O'Meara, p., Orthopaedic Review, The Basic Science of Meniscus Repair, Jun. 1993, pp. 681-686.

Okuda et aL, J of Arthroscopic and Related Surgery, Meniscal Rasping for Repair of Meniscal Tear in the Avascular Zone, vol. 15(3),1999, pp. 281-286.

S.W. Pok, et.al, In vitro characterization of polycaprolactone matrices generated in aqueous media, Acta Biomater. Mar. 2010 ; 6(3): 1061-1068.

Sgaglione et at., J. of Arthroscopic and Related Surgery, Current Concpets in Meniscus Surgery Resection to Replacement, vol. 19(10), 2003, pp. 161-188.

Smith & Nephew Technique Plus Illustrated Guide—Meniscal Repair with the FasT-Fix Suture System.

Stamboulis et al., "Mechanical properties of biodegradable polymer sutures coated with bioactive glass", Journal of Materials Science: MAterials in Medicine 13 (2002) 843-848.

Supplementary European Search Report dated Jul. 28, 2008 in connection with corresponding European Application No. EP 05 73 9944.

U.S. Appl. No. 10/983,236.

Zhang et at., Am. J. of Sports Medicine, Repairs by Trephination and Suturing of Longitudinal Injuries in the AvascularArea of the Meniscus in Goats, vol. 23(1), 1995, pp. 35-41.

W.D. Kingery, Introduction to Ceramics, Wiley Series on the Science and Technology of Materials, 1st Ed, Hollowman, J.H., et al. (EDs.), Wiley & Sons, 1960, p. 409-417.

Gomez-Vega et al., "Bioactive Glass Coatings with Hydroxyapatite and Bioglass Particles on Ti-based Implants, 1. Processing," Biomaterials, Jan. 2000, pp. 105-111, vol. 21.

Extended European Search Report for Application No. EP17169126.4 dated Oct. 10, 2017.

Horning et al. (Journal of Materials Chemistry, 19, 3838-3840, 2009) Synthetic polymeric nanoparticles by nanoprecipitation.

* cited by examiner

BIOACTIVE SOFT TISSUE IMPLANT AND METHODS OF MANUFACTURE AND USE THEREOF

CROSS-REFERENCE TO RELATED APPLICATIONS

This application claims the benefit of the filing date of U.S. Provisional Patent Application No. 62/330,584 filed May 2, 2016, the disclosure of which is hereby incorporated herein by reference. This application is related to U.S. patent application Ser. No. 15/234,239 filed Aug. 11, 2016, published as U.S. Patent Application Publication No. 2017/0043052 A1, the disclosure of which is hereby incorporated herein by reference.

FIELD OF THE INVENTION

The present invention relates to bone suture anchors, and more particularly, to bioactive suture anchors and the preparation thereof.

BACKGROUND OF THE INVENTION

Surgical sutures and suture anchors are used to close or hold together various types of soft tissue, including but not limited to skin, blood vessels, and internal organ tissue. In many instances, such sutures as well as all-suture suture anchors are made of biocompatible materials such as but not limited to non-absorbable materials such as cellulose (cotton, linen), protein (silk), processed collagen, nylon, polyester, polypropylene, aromatic polyamides ("aramid"), polytetraflourethylene, steel, copper, silver, aluminum, various alloys and the like, including many proprietary polymers and composites, to bioabsorbable (or biodegradable or bioerodible) synthetic materials, such as polymers and copolymers of glycolic and lactic acid. In some instances, such sutures have been coated with materials that provide additional benefits including antimicrobial, tribological properties, further biocompatible properties, and as well as materials that have properties to promote tissue growth and repair, including biodegradable matrices of growth factor molecules.

These suture and coating combinations often do not satisfy their desired efficacy as coatings are either removed during insertion of coated sutures due to abrasive contact with neighboring tissue or are rapidly degraded and diffused into the body before the coating can exert significant beneficial effects at the target site. Supplying high concentrations of bioactive material to the target site is not an effective solution as such concentrations may negate the benefits and indeed could be harmful, and further are relatively costly.

Attempting to address these issues, complex suture designs have utilized a multifilament biodegradable porous core surrounded by a biodegradable braided or woven sheath in which a concentration of living cells are retained within interstices disposed between the filaments of the core. In such designs, the sheath inhibits migration of the living cells from the porous core.

These designs require a concentration of bioactive material such as living cells and therapeutic agents throughout the cores and thus cannot be used with standard sutures as cores. Accordingly, other methods of preparation are needed to provide biocompatibility and tissue growth promotion benefits to surgical sutures and anchors made of suture material.

BRIEF SUMMARY OF THE INVENTION

In accordance with an aspect, a bioactive filamentary structure includes a sheath coated with a mixture of synthetic bone graft particles and a polymer forming a scaffold structure. In some arrangements, the synthetic bone graft particles may include bioactive (BA) glass and the polymer may include polycaprolactone (PCL). In some arrangements, a layer of the synthetic bone graft particles may be generally above a layer of the polymer. In some other arrangements, a layer of the synthetic bone graft particles may be generally below the layer of the polymer. In some such arrangements, at least some of the synthetic bone graft particles may extend and be exposed through the layer of the polymer to promote bone ingrowth upon insertion of the bioactive filamentary structure into a bone hole at a surgical repair, i.e., treatment, site.

In some arrangements, the bioactive filamentary structure may define a lumen through which a filament, which may be a suture or other thread-like material, may be passed. In some such arrangements, the bioactive filamentary structure may be constructed of synthetic material (e.g., PLGA, UHMWPE, or the like) or of organic material (silk, animal tendon, or the like).

In accordance with another aspect, a bioactive filamentary structure may be formed. Synthetic bone graft particles may be applied around a filamentary structure. A polymer solution may be applied around the filamentary structure. A polymer may be precipitated from the polymer solution such that the synthetic bone graft particles and the polymer may coat the filamentary structure.

In some arrangements, the synthetic bone graft particles may be applied around the filamentary structure by placing the filamentary structure into a container of synthetic bone graft particles and subsequently removing the filamentary structure from the container. In some such arrangements, the container of the synthetic bone graft particles may be shaken during placement of the filamentary structure into the container. In some such arrangements of applying the synthetic bone graft particles around the filamentary structure, the filamentary structure may be disposed on an inserter, which may be used for later placement of the filamentary structure, for handling of the filamentary structure during placement of the filamentary structure into the container of the synthetic bone graft particles.

In some arrangements, the polymer solution may be applied around the filamentary structure prior to applying the synthetic bone graft particles around the filamentary structure. In some such arrangements, the polymer solution may be applied directly to the filamentary structure. In some such arrangements of applying the polymer solution around the filamentary structure, the polymer solution may be sprayed around the filamentary structure. In other arrangements, the synthetic bone graft particles may be applied directly to the filamentary structure prior to applying the polymer solution around the filamentary structure.

In some arrangements, the synthetic bone graft particles used in forming the bioactive filamentary structure may include either of or both a calcium phosphate and a bioactive additive. In some arrangements of the synthetic bone graft particles, the bioactive additive may be but is not limited to being bioactive glass, bone chips, demineralized bone chips or powder, living cells, lyophilized bone marrow, collagen, other bioactive proteins or growth factors, biologics, peptides, glycosaminoglycans, anti-inflammatory compounds, antibiotics, anti-microbial elements, and mixtures of the foregoing. In some arrangements of the synthetic bone graft particles, the calcium phosphate may be but is not limited to being tetra-calcium phosphate, di-calcium phosphate, dicalcium phosphate dihydrous, dicalcium phosphate anhydrous, tri-calcium phosphate, mono-calcium phosphate, β-tricalcium phosphate, α tricalcium phosphate, oxypatite, hydroxypatite, and mixtures of any of the foregoing.

In some arrangements, the polymer precipitated from the polymer solution used in forming the bioactive filamentary structure may be but is not limited to being polycaprolactones (PCL), polyglycolides (PGA), polylactic acids (PLA), polyethylene, polypropylene, polystyrene, poly(D,L-lactic-co-glycolide) (PLGA), polyglycolic acid (PGA), poly-L-Lactic acid (PL-LA), polysulfones, polyolefins, polyvinyl alcohol (PVA), polyalkenoics, polyacrylic acids (PAA), polyesters, lower alkyl cellulose ethers, methylcellulose, sodium carboxymethyl cellulose, hydroxyethyl cellulose, hydroxypropyl cellulose, hydroxypropylmethylcellulose, carboxymethyl cellulose, and mixtures of any of the foregoing.

In some arrangements, the polymer solution used in forming the bioactive filamentary structure may include at least one solvent. The solvent may be but is not limited to being glacial acetic acid (GAA), acetic acid, anisole, chloroform, methylene chloride, acetylchloride, 2,2,2 trifluoroethanol, trifluoroacetic acid, 1,2-Dochloroethane, and mixtures of any of the foregoing. In preferred arrangements, the polymer solution may contain polycaprolactone (PCL) and glacial acetic acid (GAA).

In some arrangements of forming the bioactive filamentary structure, the polymer may be precipitated from the polymer solution by applying to the polymer solution a precipitating agent. The precipitating agent may be but is not limited to being sodium phosphate buffer, water, ethanol, 1-propanol, isopropyl ether, 2-butanol, hexane, and mixtures of any of the foregoing.

In some arrangements of forming the bioactive filamentary structure, the polymer may be precipitated from the polymer solution by immersing the polymer solution in a precipitating agent after applying both the synthetic bone graft particles and the polymer solution around the filamentary structure.

In some arrangements of forming the bioactive filamentary structure, the polymer may be precipitated from the polymer solution by applying a first buffer to the polymer solution after the polymer solution is applied around the filamentary structure. In this manner, the polymer solution may be partially neutralized.

In some arrangements of forming the bioactive filamentary structure, a second buffer may be applied to the polymer solution after the first buffer is applied around the filamentary structure to further dilute the polymer solution. In some such arrangements, the first and the second buffers may be sodium phosphate buffers.

In some arrangements of forming the bioactive filamentary structure, the coated filamentary structure may be dried at least after the application of the first buffer to the polymer solution. In some such arrangements, the coated filamentary structure may be dried after the application of the second buffer to the polymer solution.

In some arrangements of forming the bioactive filamentary structure, the coated filamentary structure may be placed into and may be sealed within sterile packaging, preferably after the coated filamentary structure is dried.

In some arrangements, the coated filamentary structure may be disposed on an inserter used for placing the coated filamentary structure into a treatment site. In some such arrangements, the coated filamentary structure disposed on the inserter may be placed into and may be sealed within sterile packaging, preferably after the coated filamentary structure is dried.

In accordance with another aspect, a bioactive filamentary structure may be formed. In this aspect, synthetic bone graft particles may be mixed with a polymer solution to form a scaffold mixture. The scaffold mixture may be applied around a filamentary structure. A polymer may be precipitated from the polymer solution such that the synthetic bone graft particles and the polymer coat the filamentary structure.

In accordance with another aspect, a bioactive filamentary structure may include a filamentary structure, synthetic bone graft particles, and a polymer. The synthetic bone graft particles may coat the filamentary structure. The polymer may partially coat the synthetic bone graft particles such that at least some of the bone graft particles may be at least partially exposed through the polymer coating. In some arrangements, the filamentary structure may be an all-suture suture anchor. In some arrangements, the bone graft particles exposed through the polymer coating may extending from the filamentary structure beyond the polymer coating.

BRIEF DESCRIPTION OF THE DRAWINGS

These and other features, aspects, and advantages of the present invention will become better understood with regard to the following description and accompanying drawings in which.

DETAILED DESCRIPTION

As used herein, the term "filament" and like terms are inclusive of single or multiple strands, threads, fibers, strings, wires or sutures in which such terms preferably refer to a suture or other thread-like material, and in particular a braided suture, having a hollow core along at least a portion of its length. A filament may be constructed from homogenous or heterogeneous materials such as, but not limited to, polyester, polyethylene (including ultra-high molecular weight polyethylene (UHMWPE)), polytetrafluoroethylene (including expanded polytetrafluorethylene), nylon, polypropylene, aramids (such as Kevlar-based materials), polydioxanone, polygycolic acid, liquid crystal polymer (LCP), organic material (silk, animal tendon, or the like), metallic wire, or any combination of these materials.

Figure 1:
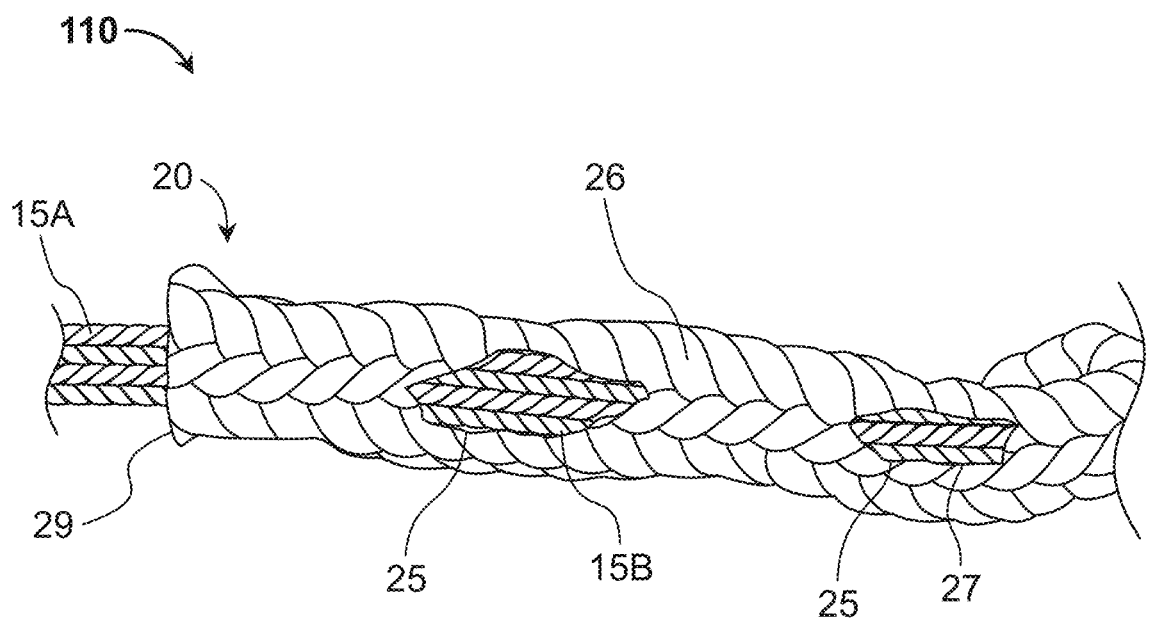
FIG. 1 is a perspective view of a sheath and filament combination of the prior art.

Referring now to the drawings, as shown in FIG. 1, sheath and filament combination 10 known in the art forms an all-suture suture anchor that includes first filament 15A and second filament 15B, which in some arrangements may be a monofilament while in other arrangements may be a braided suture as shown, and sheath 20 having an inner lumen defined by inner surface 27 of the sheath through which the filament is inserted. Preferably, each of sheath 20 and the filaments 15A, 15B are composed of suture, and specifically a blend of UHMWPE and polyester. Sheath 20, which may be but is not limited to being a sheath of an all-suture suture anchor for use as part of the ICONIX® All Suture Anchor System, includes openings 25 along its length that expose filaments 15A, 15B and allow the sheath to fold upon itself and to compress when opposing portions of the filament are pulled in a direction away from the sheath while the sheath is held, such as by a patient's bone or other tissue, at its ends. This deformation of the sheath drastically changes an aspect ratio of the sheath to provide a resistance to pullout when the suture is inserted into a prepared bone hole (see FIG. 4B for an example of this deformation being applied to prepared sheath 120 prepared in accordance with an embodiment of the present invention), as described in U.S. Pat. No. 9,445,803 to Marchand et al. ("the '803 Patent"), which is hereby incorporated by reference in its entirety herein.

Figure 2:
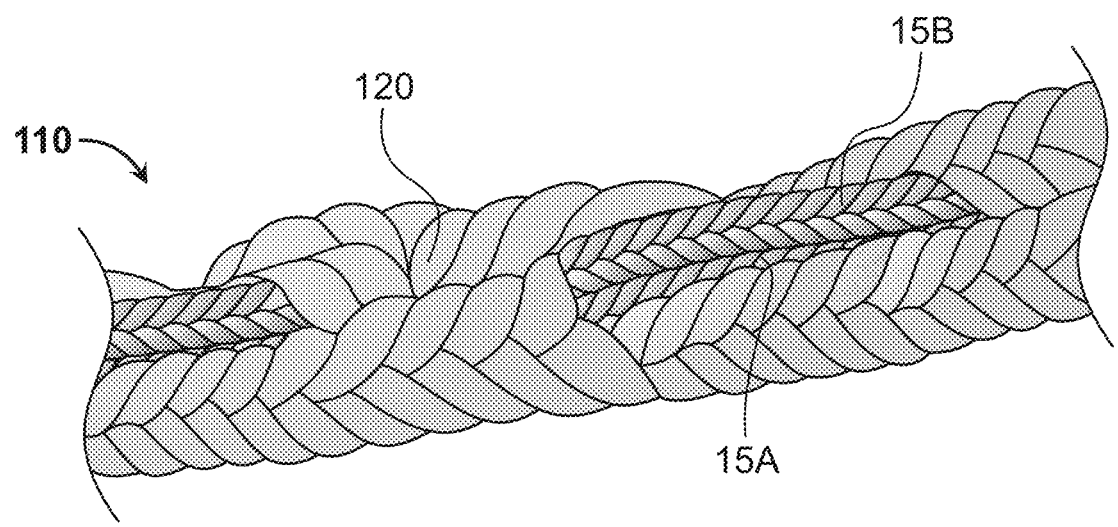
FIG. 2 is a perspective view of a sheath and filament combination in accordance with an embodiment.

As shown in FIG. 2, sheath and filament combination 110 includes first filament 15A, second filament 15B, and prepared sheath 120 having an inner lumen through which the filament is inserted. Prepared sheath 120 is generally formed by applying synthetic bone graft particles, which may be but are not limited to being bioactive (BA) glass or calcium phosphate particles, onto and within sheath 20 and then coating the synthetic bone graft particles with a polymer coating layer, which may be but is not limited to being a layer of polycaprolactone (PCL). The PCL acts as a barrier or otherwise secures the synthetic bone graft particles to prevent migration and rapid degradation and diffusion of the bone graft particles upon insertion of sheath and filament combination 110 into a treatment site.

Figure 3A:
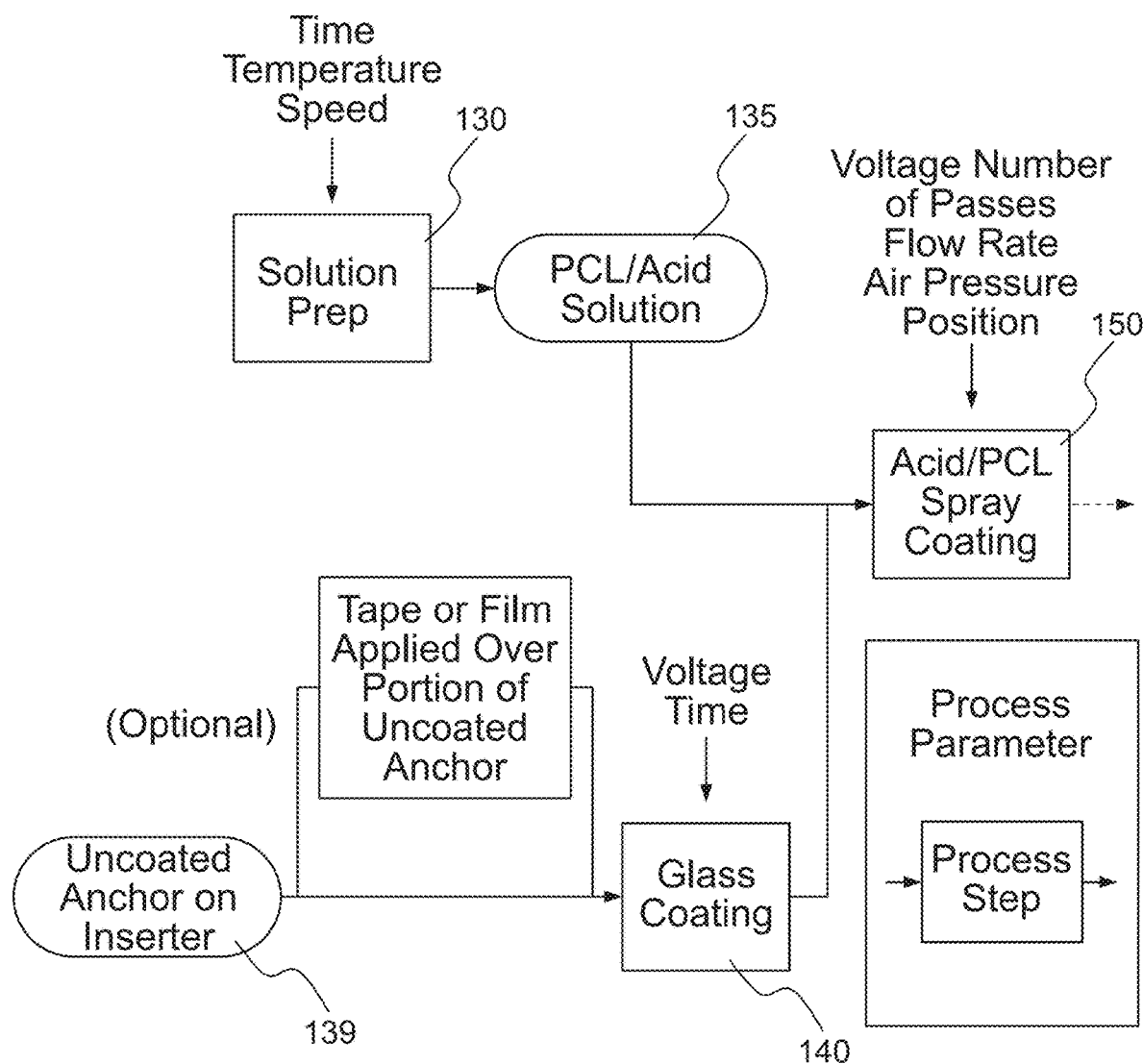
FIGS. 3A and 3B are portions of a process flow diagram for preparing the sheath and filament combination shown in FIG. 2.
Figure 3B:
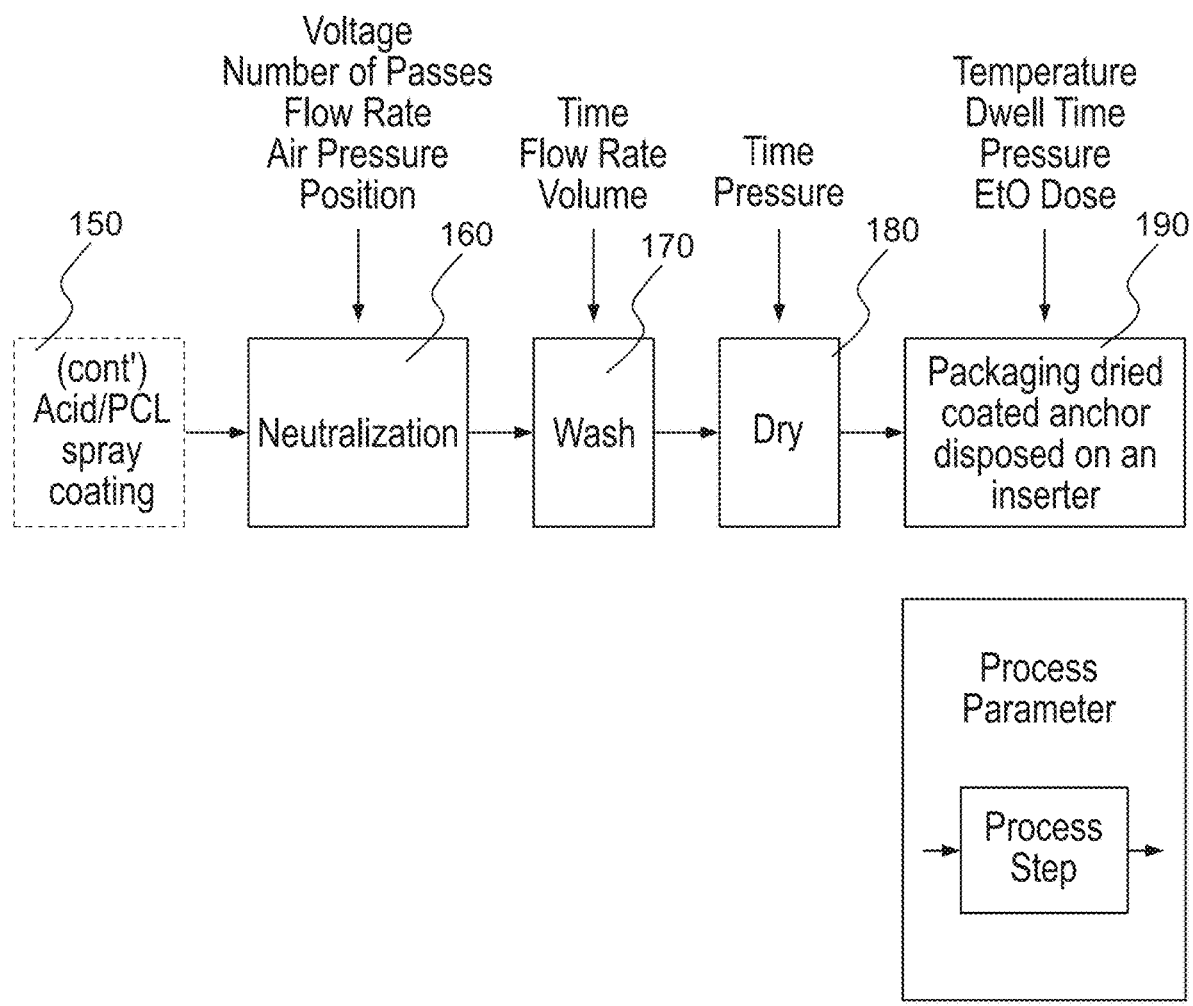

Referring now to FIGS. 3A and 3B, in step 130, polymer solution 135 containing the polymer coating and a solvent in which the polymer coating may be soluble, which preferably may be acetic acid (AA) and more preferably may be glacial acetic acid (GAA), may be prepared by mixing the polymer coating in the solvent at an appropriate temperature for an appropriate time. In preferred arrangements, the polymer may be fully dissolved in the solvent. In one example, to form polymer solution 135, the mixture of the polymer and the solvent preferably may be placed on a heated plate, such as but not limited to the plate of an orbital shaker, set at a temperature in the range of approximately 30° C. to— approximately 55° C. for a time preferably less than 24 hours, or otherwise up until a time the polymer fully dissolves.

Once prepared, the molecular weight (MW) of the polymer coating may be but is not limited to being in the range of 33-117 kilodaltons (kDa). In general, greater MWs of the polymer coating will lead to greater bioactivity at a treatment site but will cause slower resorbability. However, bioactivity may vary with other variables such as but not limited to any of the amount, size, and surface area of the synthetic bone graft particles, coating thickness and porosity. In preferred arrangements, the concentration of polymer solution 135 may be in the range of about 5% to about 16% mass per unit volume, and preferably approximately 5%. The viscosity of polymer solution 135 may be desirably in the range of approximately 1 to approximately 30 centipoise (cP), and preferably about 20 cP. Within this viscosity range, polymer solution 135 may have sufficient flowability for application to sheath 20 while at the same time have sufficient adhesion characteristics to inhibit sliding of the solution off of the sheath after application. Alterations in concentration and molecular weight of polymer solution 135 may have an effect on droplet size, spray pattern, and the characteristics of the polymer coating after being applied to sheath 20.

In parallel with the preparation of polymer solution 135, sheath 20 is coated with synthetic bone graft particles, which may be but are not limited to being BA glass particles, at step 140. In some arrangements, sheath 20 may be held horizontally (i.e., parallel to the floor), such as by an operator or a robotic arm, and dipped into a container containing the bone graft particles. In such arrangements, openings 25 of sheath 20 may be oriented vertically upward (i.e., face away from the floor) during dipping of the sheath into the container such that the synthetic bone graft particles contact and enter only or at least mainly outer surface 26 (as illustrated in FIG. 1) of the sheath. In alternative arrangements, sheath 20 may be held in any other orientation, including vertically in which when the sheath is dipped into the container of the synthetic bone graft particles, such particles may coat at least a portion of inner surface 27 (identified in FIG. 1) of the sheath and may be held on the anchor by ionic forces, van der Waals' forces and physical entrapment between bone graft particles. Such interactions may be generated by static electricity caused by friction between the bone graft particles and the sheath during the dipping of the sheath. In some arrangements, the bone graft particles may be held mechanically by being placed in the interstices of the fibers of the sheath. In some alternative arrangements, a resistive mask (not shown), which may be but is not limited to being a tape, film, or other covering, may be applied over central openings 25 and end openings 29 of sheath 20 to prevent or at least inhibit the intrusion of synthetic bone graft particles into the inner lumen of the sheath defined by inner surface 27 of the sheath. In some arrangements, the resistive mask may prevent friction between first filament 15A and second filament 15B.

In preferred arrangements, sheath 20 may be dipped into the synthetic bone graft particles while surrounding filaments 15A, 15B as part of sheath and filament combination 10, while in other arrangements, sheath 20 may be separated from either or both of filaments 15A, 15B during the graft coating process. In arrangements in which sheath 20 is oriented with either of or both central openings 25 and end openings 29 exposed to the synthetic bone graft particles, at least a portion of either of filaments 15A, 15B may be coated with the synthetic bone graft particles along with sheath 20. To avoid coating either or both of filaments 15A, 15B or allowing synthetic bone graft particles to be incorporated between either of the filaments and the interior of sheath 20, a resistive mask (not shown) may be applied to the sheath over openings 25 during application of the synthetic bone graft particles onto the sheath. Reducing these particles in these areas may avoid introducing additional friction when sliding filaments 15A, 15B through sheath 20 after insertion of sheath and filament combination 10 into a prepared bone hole at a treatment site.

As shown in FIG. 3A, at step 139 prior to step 140, sheath and filament combination 10 may be placed onto an inserter (not shown), such as the inserter described in the '803 Patent or the inserter described in either of U.S. Pat. No. 8,821,494 B2 to Pilgeram and U.S. Patent Application Publication No. 2014/0039552 A1 to Pilgeram, the disclosures of each of which are hereby incorporated by reference herein. In this manner, the inserter may be held by the respective operator or robotic arm during placement of sheath 20, or in some arrangements sheath and filament combination 10, into the container of synthetic bone graft particles. Placing sheath 20 onto the inserter prior to loading with synthetic bone graft particles avoids any loss of the particles that may otherwise occur during such placement of the sheath. The particle size of the synthetic bone graft particles applied to sheath 20 is preferably in the range from about 32 µm to about 90 µm. Larger or smaller particles sizes are possible in which smaller particle sizes drive more bioactivity at a treatment site but may be resorbed too quickly for certain applications.

In some arrangements, the container of synthetic bone graft particles may be in the form of a bowl or cup, such as but not limited to a glass, plastic, or metal bowl. In some arrangements, either of or both the container and sheath 20 (and in some instances, the inserter and filament 15 as described previously herein) may be vibrated to prevent or inhibit agglomeration of the particles and to achieve an appropriate graft coating mass for a particular anchor size. In some arrangements, the container may be rotated, i.e., spun, and may be translated along with being vibrated. Vibration, translation, and rotation of the container allows the synthetic bone graft particles to uniformly, thoroughly, and continuously contact the outer surface of sheath 20. In this manner, the bone graft particles may coat sheath 20 and become wedged at location 140A between fibers forming the sheath. (See FIGS. 5A and 5B.) The frequency and amplitude of either of or both the vibration and rotation may be altered by changing a corresponding voltage setting on a vibration fixture, which may be but is not limited to being a vibration table. These settings along with the time of vibration affect the mass of the synthetic bone graft particles applied to sheath 20. In this manner, the synthetic bone graft particles may be embedded between the fibers of sheath 20, and preferably agglomerates at pics of the fibers of the anchor. Sheath 20 may be tensioned and compressed along an axis, e.g., its longitudinal axis, to open the fibers of the sheath. In this manner, the synthetic bone graft particles may be set in between the fibers. Alternatively, sheath 20 may any of be vibrated, translated, and rotated relative to the container in order to coat the sheath with the synthetic bone graft particles. In some arrangements, after graft particles are applied to sheath 20, the sheath (along with filament 15 and the inserter if attached to the sheath) may be shaken to remove loose particles.

With reference to step 150 shown in FIG. 3A, graft-coated sheath 20 may be coated with polymer solution 135. Polymer solution 135 may coat, in one example, at least 30% of the outer surface of graft-coated sheath 20, in another example, at least 70% of the outer surface of graft-coated sheath, and, in still another example, at least 90% of the outer surface of graft-coated sheath, although in some arrangements, the polymer solution may coat less than 30% of the outer surface of the graft-coated sheath. In the example shown, polymer solution 135 may be sprayed, for example in the form of a mist, from a nozzle (not shown) onto some, or preferably all exposed areas, of graft-coated sheath 20. In some arrangements, the sprayer may be mechanical sprayer, in which the flow rate provided by the sprayer may be altered by increasing or decreasing the restriction within the nozzle of the sprayer. In other arrangements, the sprayer may be part of an ultrasonic spray system, e.g., the Sono-tek ExactaCoat SC ultrasonic spraying system, which includes an ultrasonic spray nozzle used in conjunction with an air stream directed to the nozzle and controlled with a gantry system, which may be operated by server motors, or other motion control system. In such arrangements, the flow rate of the spray as it exits the nozzle may be altered as desired by adjusting the voltage to piezoelectric transducers to create vibrations against and to cause the atomization of polymer solution 135 as it flows.

The flow rate of the spray, the local air pressure around the spray, the distance of the exit of the nozzle from graft-coated sheath 20 (or uncoated sheath 20 in other embodiments such as in the formation of prepared sheath 220 described further herein), the speed of the exit of the nozzle itself relative to the sheath, and the number of passes over an area or areas of the sheath all affect the thickness of polymer solution 135 applied to the graft-coated (or uncoated) sheath. Preferably, polymer solution 135 should not be too thin when applied to graft-coated (or uncoated) sheath 20 such that the solution does not sufficiently adhere to the respective coated (or uncoated) sheath. Conversely, polymer solution 135 should not be too thick such that either of or both sheath and filament combination 110 is too stiff and prepared sheath 120 (or other prepared sheath, such as prepared sheath 220) defines a maximum outer perimeter that is greater than an inner perimeter of a prepared bone hole into which the sheath is to be inserted and thus is susceptible to removal of the applied synthetic bone graft particles during such insertion.

Referring now to FIG. 3B, during step 160, polymer solution 135 coating sheath 20 is exposed to a precipitating agent, which may be but is not limited to being a sodium phosphate buffer composed of sodium monobasic and sodium dibasic in water ($Na_2HPO_4$ and $NaH_2PO_4$) or other neutral pH solution, which causes precipitation of the polymer coating from polymer solution 135 such that the polymer coating may coat the bone graft particles of prepared sheath 20 in order to retain the particles and prevent their premature degradation when prepared sheath 120 is inserted into a treatment site. In preferred arrangements, sheath 20 coated with solution 135, which in more preferred arrangements may be disposed on an inserter as discussed previously herein, is dipped into a reservoir containing the precipitating agent. In some alternative arrangements, the precipitating agent may be sprayed onto sheath 20 coated with polymer solution 135. Under certain of the conditions of the nozzle listed above with respect to the thickness of polymer solution 135, a stream, i.e., a fluid jet, of 10 mL to 20 mL of the buffer solution may be rapidly applied for less than approximately 30 seconds to sheath 20 prepared with polymer solution 135, again which in more preferred arrangements may be disposed on an inserter as discussed previously herein. In any of these arrangements, sheath 20 when coated with polymer solution 135 preferably is soaked or otherwise saturated with the precipitating agent immediately after application of polymer solution 135 in order to more evenly distribute the polymer solution and to reduce the exposure of the polymer solution, the synthetic bone graft particles when such particles are coating sheath 20, and the sheath itself to acidic conditions.

During step 170 and following precipitation step 160, sheath 20 coated with the polymer coating and remaining polymer solution 135 is washed, such as by but not limited to being by either of or both a sodium phosphate buffer and deionized (DI) water ("wash solution"). In this manner, residual salts that have formed, which may be acetate and phosphate salts from the GAA (or other form of AA) solvent used in polymer solution 135 and the sodium phosphate buffer used at step 160, are reduced to a physiologically acceptable range. In preferred arrangements, sheath 20 coated with the polymer coating and remaining polymer solution is washed in a bath containing the wash solution.

The combination of precipitation step 160 and washing step 170 under proper conditions should yield a residual amount of the GAA (or other form of AA) solvent of preferably less than approximately 0.040 molar (M). Use of the buffer as or in the washing solution neutralizes the pH of the coating on sheath 20 more quickly during processing than water alone and thus prevents unnecessary erosion of the synthetic bone graft particles otherwise caused by the GAA (or other form of AA) solvent.

As further shown in FIG. 3B, during step 180, sheath 20 coated with the precipitated polymer coating covering the applied synthetic bone graft particles is subjected to drying to form prepared sheath 120 and to remove any residual GAA (or other form of AA). In this manner, degradation of the synthetic bone graft particles and polymer coating due to the GAA (or other form of AA) during packaging may be prevented to extend the shelf life of sheath 120. Preferably, drying step 180 may be conducted without the addition of heat when used with polymers having low melting points, such as but not limited to PCL having a melting point of or approximately 60° C. In some preferred arrangements, coated sheath 20 may be dried by vacuum to quickly remove any moisture and residual acid while preserving the integrity of the synthetic bone graft particles and resultant polymer coating. It is also possible to dry coated sheath 20 with air at atmospheric pressure or forced air at an elevated pressure. Supplying compressed or otherwise forced air to coated sheath 20 is also less preferable than applying a vacuum as a sufficient amount of air to remove an acceptable amount of moisture may cause some of the polymer coating or synthetic bone graft particles to be removed from sheath 20. Following drying step 180, the moisture content within the polymer coating is preferably less than approximately 0.5% wt, and the synthetic bone graft particles are firmly adhered to sheath 20 by the remaining polymer coating. Optionally, prior to or, in some arrangements, in place of drying step 180, sheath 20 may be dried by way of moisture wicking through a capillary effect via direct contact with moisture on the sheath using a porous-like structure, such as but not limited to a brush, a cloth or paper towel, by way of a desiccant, or by way of another acceptable and preferably biocompatible drying agent known to those of ordinary skill in the art.

In preferred arrangements, after precipitation and drying of the polymer coating, the thickness of the polymer coating of prepared sheath 120 (or other prepared sheath such as prepared sheath 220) preferably may be in the range of less than approximately 100 μm, and more preferably in the range of 1 μm to 30 μm. As such, the polymer coating may have a thickness such that a significant number of synthetic bone graft particles coating sheath 20 are partially exposed, at their apices, through the polymer coating in addition to their exposure through the pores of the polymer coating. By way of this exposure, bioactivity may occur shortly after placement of prepared sheath 120 at a treatment site.

Figure 4A:
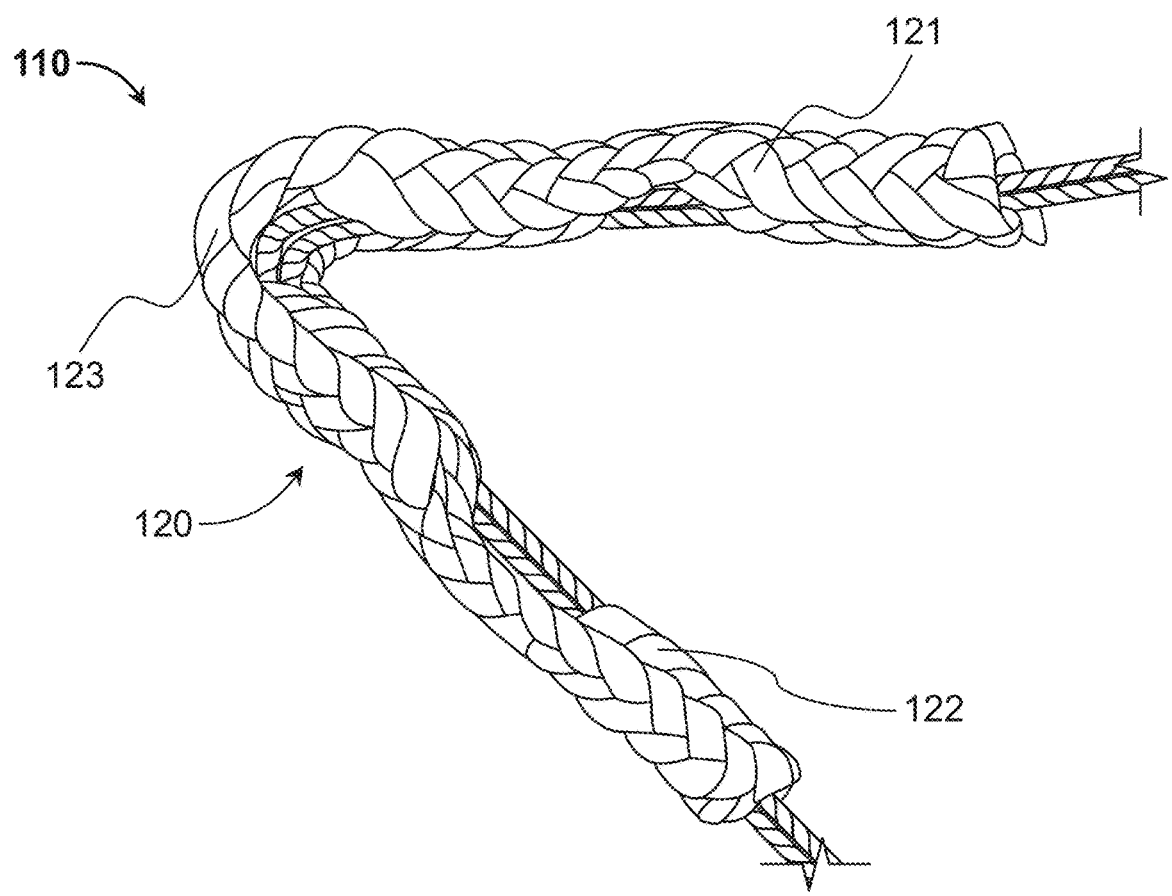
FIGS. 4A and 4B are perspective views of the sheath and filament combination shown in FIG. 2 in pre-deployment and deployed states.
Figure 4B:
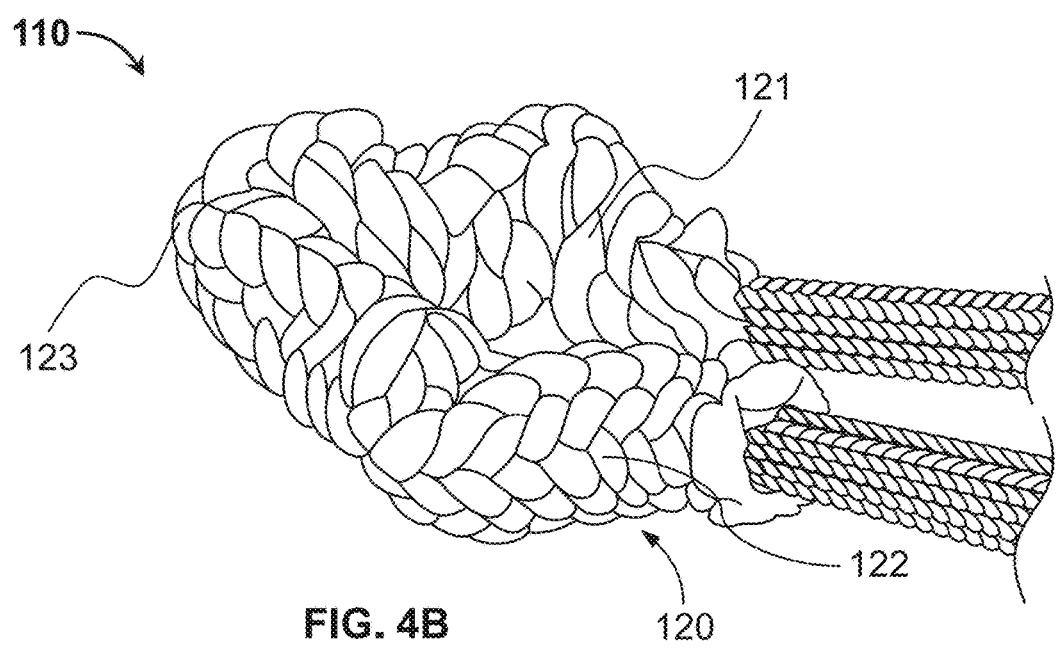

Referring now to FIG. 4A, when initially prepared as sheath and filament combination 110 placed onto the inserter, prepared sheath 120 is folded onto itself such that opposing portions 121, 122 of the prepared sheath, which may be in the form of legs, extend from end 123 in substantially parallel directions to each other. As shown in FIG. 4B, when deployed, prepared sheath 120 compresses, i.e., bunches, such that opposing portions 121, 122 are pushed in transverse directions to the inserter and away from each other, forming a substantially clover-like shape. In this deployed, compressed state, portions of the polymer coating may any of break up, crack, and stretch, providing further exposure of the synthetic bone graft particles and thus providing for greater bioavailability.

As further shown in FIG. 3B, during step 190, prepared sheath 120 is inserted into sterile packaging. In some arrangements, prepared sheath 120 may be placed into a pouch, which may be but is not limited to being made of aluminum foil, with a covering or leader, which may be but is not limited to being an olefin sheet such as but not limited to Tyvek® olefin sheets by E. I. du Pont de Nemours and Company. In some arrangements, the sheath (or sheath and filament combination) inserter described previously herein may be placed into the pouch with prepared sheath 120 disposed on the inserter and ready for placement into a treatment site. In alternative arrangements, prepared sheath 120 (or sheath and filament combination 110) may be separated from the inserter, and in such arrangements, the inserter may be placed in the same pouch as the sheath (or respective sheath and filament combination 110) or a separate sterile pouch. In any of these arrangements, a plurality of combinations or kits of prepared sheath 120 (or respective sheath and filament combination 110) and the inserter may be placed into sleeves. Preferably, when packaged and sterilized, the sterility assurance level (SAL) for prepared sheath 120 (or respective sheath and filament combination 110), or for the combination or kit of the sheath (or respective sheath and filament combination 110) and the corresponding inserter, is at or below $10^{-6}$ SAL To achieve this SAL, the packaged sheath 120 or packaged combination or kit of the sheath and the corresponding inserter preferably may be subjected to ethylene oxide (EtO) processing as well as periodic functional checks and lot release testing.

Figure 5A:
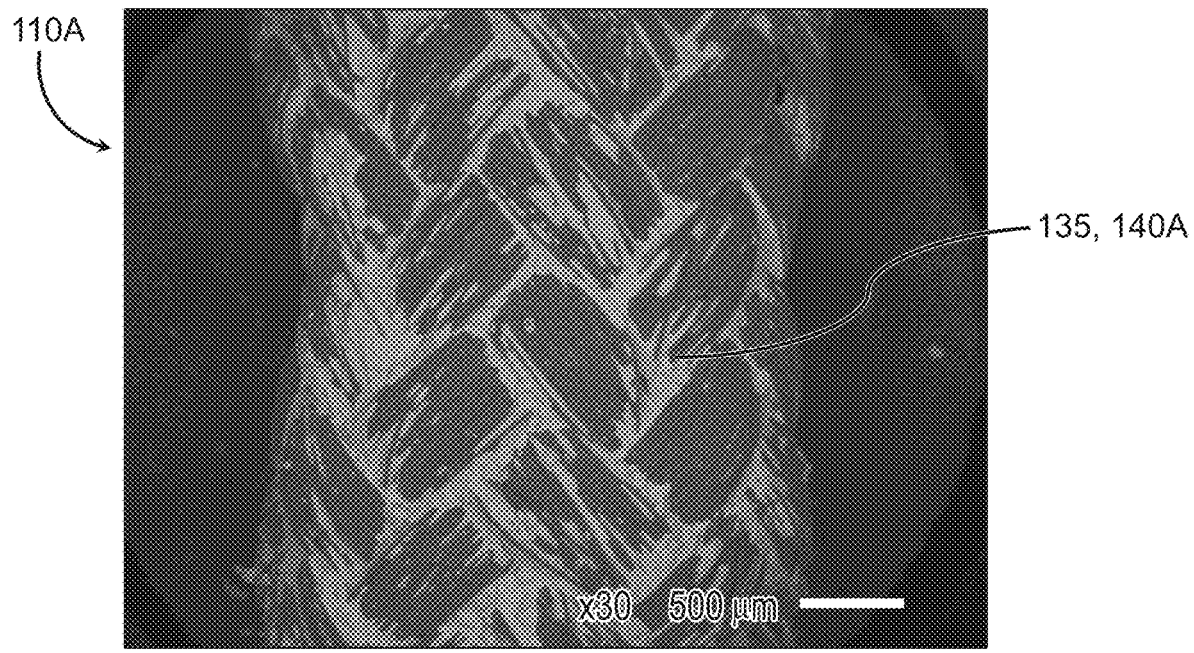
FIGS. 5A and 5B are plan views of respective portions of sheaths exposed to simulated body fluid in accordance with other embodiments.
Figure 5B:
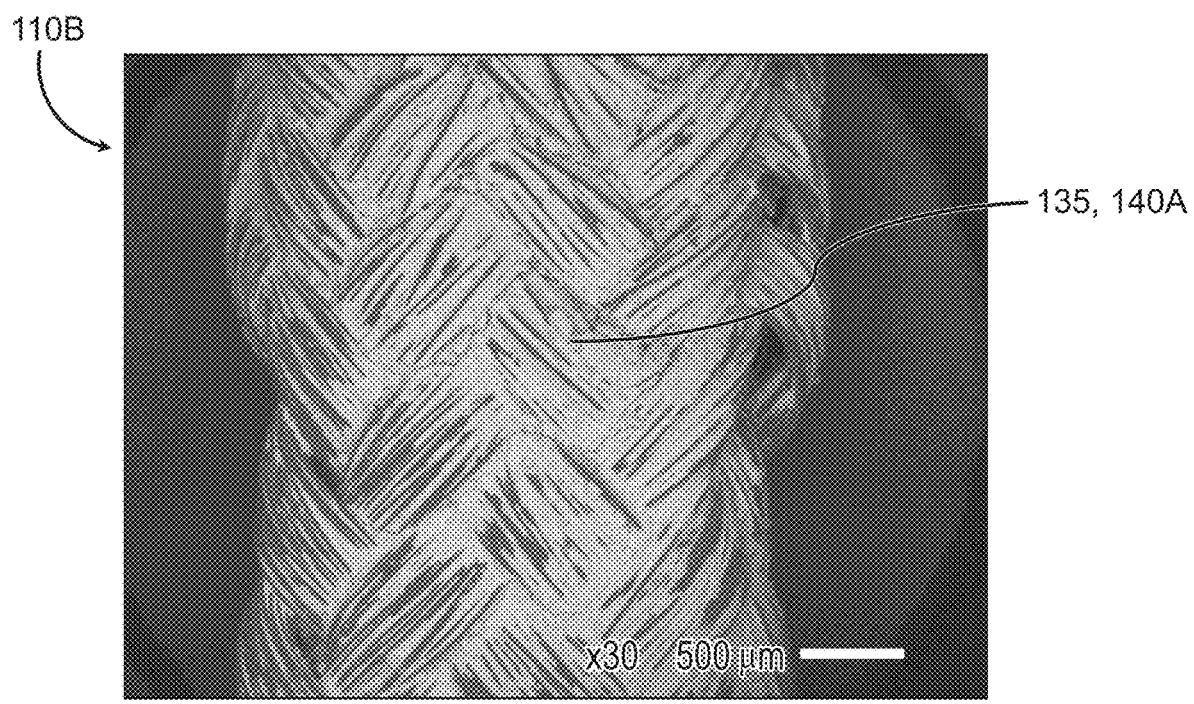

As shown in FIG. 5A, in one arrangement, sheath and filament combination 110A may be as described previously herein with respect to sheath and filament combination 110 in which the polymer coating is low molecular weight (LMW) PCL. As shown, the LMW PCL leads to hydroxyapatite deposition and crystallization (shown in whitish gray) on the surface of the sheath when exposed to living tissue fluids (as demonstrated through the use of simulated body fluids in the example shown), in particular at the pics, i.e., crossings, of fibers of the sheath. As shown in FIG. 5B, in another arrangement, sheath and filament combination 110B as described previously herein with respect to sheath and filament combination 110 in which the polymer coating is high molecular weight (HMW) PCL. The HMW PCL leads to hydroxyapatite deposition and crystallization (shown in whitish gray) on the surface of the sheath when exposed to living tissue fluids (as demonstrated through the use of simulated body fluids in the example shown), like the LMW PCL, but the hydroxyapatite deposition is substantially greater for the HMW PCL than for the LMW PCL, as shown by comparison of FIGS. 5A and 5B.

Figure 6:
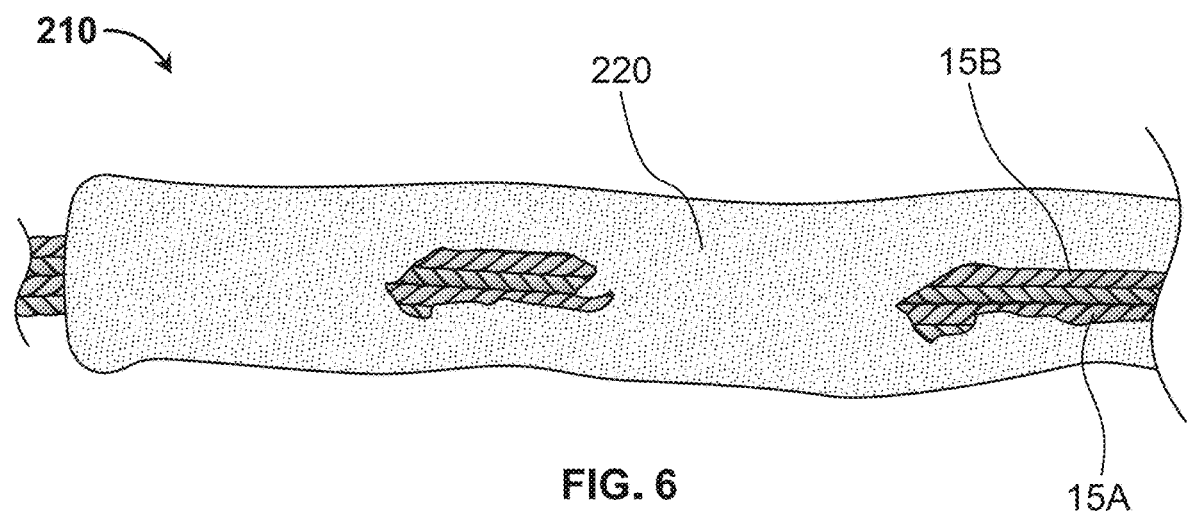
FIG. 6 is a perspective view of a sheath and filament combination in accordance with another embodiment.

Referring now to FIG. 6, in another arrangement, sheath and filament combination 210 includes first filament 15A, second filament 15B, and prepared sheath 220 having an inner lumen through which the filaments are inserted. Prepared sheath 220 is generally formed by coating sheath 20 (see FIG. 1) with a polymer coating layer and then applying synthetic bone graft particles onto the polymer-coated sheath 20. In this manner, it is possible to add more exposed synthetic bone graft particles to sheath 20.

Figure 7:
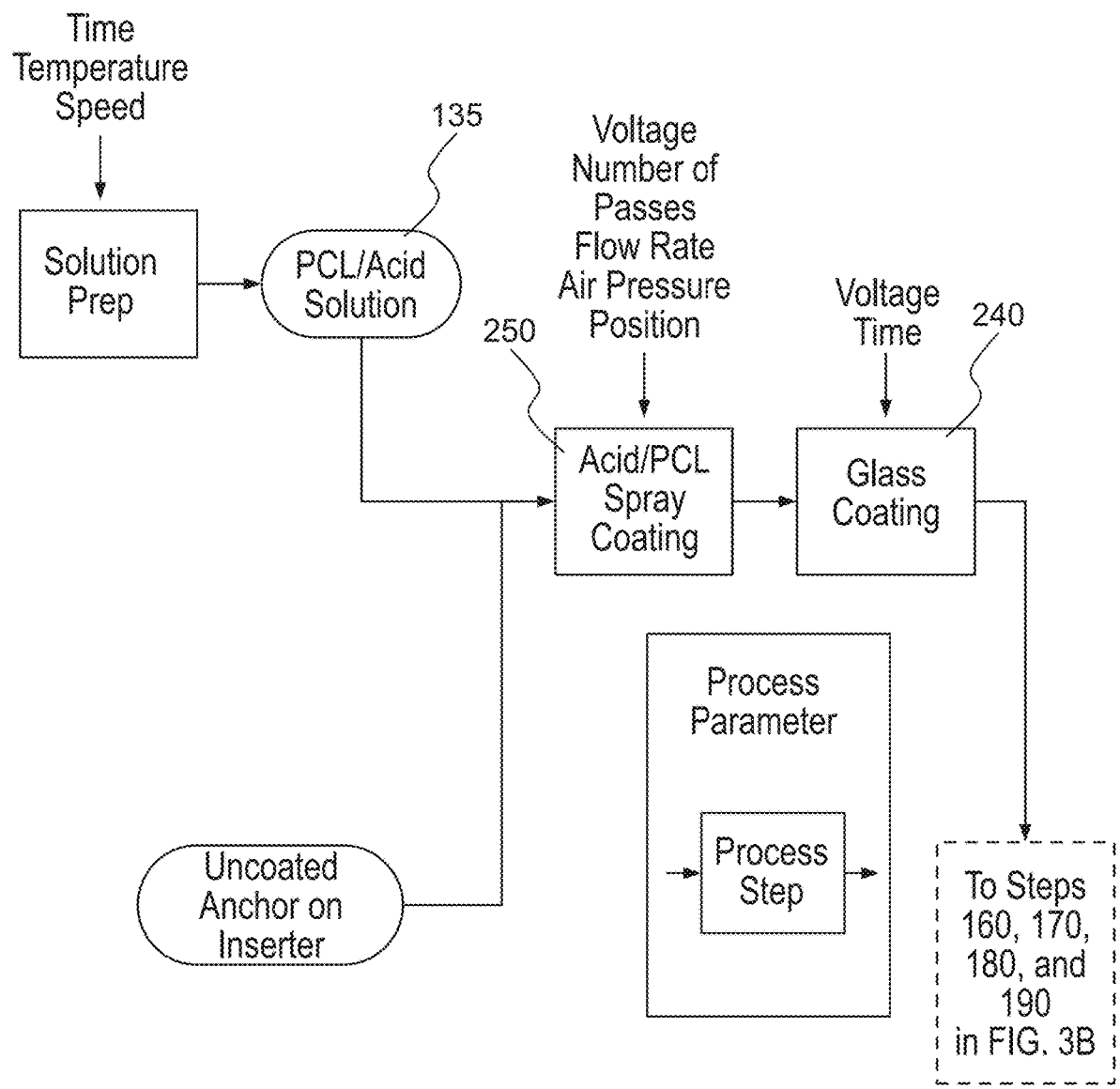
FIG. 7 is a perspective view of a portion of a process flow diagram for preparing the sheath and filament combination shown in FIG. 6.

Referring now to FIG. 7, prepared sheath 220 is formed in the same or substantially the same manner as prepared sheath 120 with two exceptions. First, polymer solution coating step 150 is replaced with polymer solution coating step 250 in which polymer solution 135 coats sheath 20 without any synthetic bone graft particles coating the sheath.

Second, graft coating step 140 is replaced with graft coating step 240 in which synthetic bone graft particles are applied to sheath 20 coated with polymer solution 135.

In some alternative arrangements, in place of or in addition to BA glass, the synthetic bone graft particles may include but are not limited to calcium phosphate or other bioactive additives. The calcium phosphate may be but is not limited to being tetra-calcium phosphate, di-calcium phosphate, dicalcium phosphate dihydrous, dicalcium phosphate anhydrous, tri-calcium phosphate, mono-calcium phosphate, β-tricalcium phosphate, α-tricalcium phosphate, oxypatite, hydroxypatite, and mixtures thereof. The other bioactive additives may include but are not limited to bone chips, demineralized bone chips or powder, living cells, lyophilized bone marrow, collagen, other bioactive proteins or growth factors, biologics, peptides, glycosaminoglycans, anti-inflammatory compounds, antibiotics, anti-microbial elements, and mixtures thereof.

In some alternative arrangements of sheath and filament combination 110, in place of or in addition to PCL, the barrier layer may be but is not limited to being replaced with another polymer such as polyglycolides (PGA), polylactic acids (PLA), polyethylene, polypropylene, polystyrene, poly (D,L-lactic-co-glycolide) (PLGA), polyglycolic acid (PGA), poly-L-Lactic acid (PL-LA), polysulfones, polyolefins, polyvinyl alcohol (PVA), polyalkenoics, polyacrylic acids (PAA), polyesters, lower alkyl cellulose ethers, methylcellulose, sodium carboxymethyl cellulose, hydroxyethyl cellulose, hydroxypropyl cellulose, hydroxypropylmethylcellulose, carboxymethyl cellulose, and mixtures thereof.

In some alternative arrangements, in place of or in addition to GAA, the coating solvent in the PCL or other polymer solution may be but is not limited to being at least one solvent of any of acetone, anisole, chloroform, methylene chloride, acetylchloride, 2,2,2 trifluoroethanol, trifluoroacetic acid, 1,2-Dochloroethane, mixtures thereof.

In some alternative arrangements, precipitating agents other than or in addition to the sodium phosphate buffer described previously herein may be used during formation of coated sheaths such as sheaths 120, 220. Such precipitating agents include but are not limited to water, ethanol, 1-propanol, isopropyl ether, 2-butanol, hexane, and mixtures thereof.

In some alternative arrangements, the combination of the polymer coating and the synthetic bone graft particles may be applied to any braided structure, especially such structures to be implanted into bone. Such braided structures may be but are not limited to ligament graft material, e.g., anterior cruciate ligament (ACL) graft material. The combination of the polymer coating and the synthetic bone graft particles may be applied to any such braided structure in the same manner that the combination of the polymer coating and the synthetic bone graft particles described previously herein as being applied to sheath and filament combination 110, 210.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the invention, and in the invention generally.

Furthermore, although the invention herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below. Moreover, the foregoing disclosure should be taken by way of illustration rather than by way of limitation as the present invention is defined by the claims set forth below.

The invention claimed is:

1. A method of forming a bioactive filamentary structure, comprising the steps of:
    applying synthetic bone graft particles around a filamentary structure;
    after the synthetic bone graft particles applying step, applying a polymer solution to the bone graft particles and around the filamentary structure; and
    after the polymer solution applying step, precipitating a polymer from the polymer solution such that the synthetic bone graft particles and the polymer coat the filamentary structure.

2. The method of claim 1, wherein the synthetic bone graft particles are applied around the filamentary structure by placing the filamentary structure into a container of synthetic bone graft particles and then removing the filamentary structure from the container.

3. The method of claim 2, wherein the container of the synthetic bone graft particles is shaken during placement of the filamentary structure into the container.

4. The method of claim 1, wherein the synthetic bone graft particles include either one or both of calcium phosphate and a bioactive additive.

5. The method of claim 4, wherein the bioactive additive is selected from the group consisting of bioactive glass, bone chips, demineralized bone chips or powder, living cells, lyophilized bone marrow, collagen, other bioactive proteins or growth factors, biologics, peptides, glycosaminoglycans, anti-inflammatory compounds, antibiotics, anti-microbial elements, and mixtures thereof.

6. The method of claim 4, wherein the calcium phosphate is selected from the group consisting of tetra-calcium phosphate, di-calcium phosphate, dicalcium phosphate dihydrous, dicalcium phosphate anhydrous, tri-calcium phosphate, mono-calcium phosphate, β-tricalcium phosphate, α-tricalcium phosphate, oxypatite, hydroxypatite, and mixtures thereof.

7. The method of claim 1, wherein the polymer is at least one selected from the group consisting of polycaprolactones (PCL), polyglycolides (PGA), polylactic acids (PLA), polyethylene, polypropylene, polystyrene, poly(D,L-lactic-co-glycolide) (PLGA), polyglycolic acid (PGA), poly-L-Lactic acid (PL-LA), polysulfones, polyolefins, polyvinyl alcohol (PVA), polyalkenoics, polyacrylic acids (PAA), polyesters, lower alkyl cellulose ethers, methylcellulose, sodium carboxymethyl cellulose, hydroxyethyl cellulose, hydroxypropyl cellulose, hydroxypropylmethylcellulose, carboxymethyl cellulose, and mixtures thereof.

8. The method of claim 1, wherein the polymer solution includes at least one solvent selected from the group consisting of glacial acetic acid (GAA), acetic acid, anisole, chloroform, methylene chloride, acetylchloride, 2,2,2 trifluoroethanol, trifluoroacetic acid, 1,2-Dochloroethane, and mixtures thereof.

9. The method of claim 1, wherein the polymer is precipitated from the polymer solution by applying to the polymer solution a precipitating agent selected from the group consisting of sodium phosphate buffer, water, ethanol, 1-propanol, isopropyl ether, 2-butanol, hexane, and mixtures thereof.

10. The method of claim 1, wherein the polymer solution is applied around the filamentary structure by spraying the polymer solution around the filamentary structure.

11. The method of claim 1, wherein the step of precipitating the polymer from the polymer solution includes immersing the polymer solution in a precipitating agent after applying both the synthetic bone graft particles and the polymer solution around the filamentary structure.

12. The method of claim 1, wherein the step of precipitating the polymer from the polymer solution includes applying a first buffer to the polymer solution after the polymer solution is applied around the filamentary structure to at least partially neutralize the polymer solution.

13. The method of claim 12, further comprising the step of drying the coated filamentary structure at least after the first buffer is applied to the polymer solution.

14. The method of claim 13, further comprising the step of packaging the dried coated filamentary structure disposed on an inserter.

15. The method of claim 12, further comprising the step of applying a second buffer to the polymer solution after the first buffer is applied around the filamentary structure to further dilute the polymer solution.

16. The method of claim 15, wherein the first and the second buffers are sodium phosphate buffers.

17. The method of claim 1, further comprising covering a portion of the filamentary structure such that the bone graft particles do not coat the covered portion of the filamentary structure during the synthetic bone graft particles applying step.

18. The method of claim 17, wherein the covering step includes applying a mask over openings defined by the filamentary structure.

19. The method of claim 18, wherein the mask is a tape or a film.

20. The method of claim 1, wherein the bone graft particles are wedged between fibers of the filamentary structure after the synthetic bone graft particles applying step.

21. A method of forming a bioactive filamentary structure, comprising the steps of:
mixing synthetic bone graft particles with a polymer solution to form a scaffold mixture;
applying the scaffold mixture around a filamentary structure;
applying a first buffer to the scaffold mixture after the scaffold mixture is applied around the filamentary structure to at least partially neutralize the polymer solution; and
precipitating a polymer from the polymer solution such that the synthetic bone graft particles and the polymer coat the filamentary structure,
wherein the bone graft particles are wedged between fibers of the filamentary structure after the scaffold mixture applying step.

22. The method of claim 21, wherein the polymer solution comprises polycaprolactone (PCL) and glacial acetic acid (GAA).

23. The method of claim 21, further comprising covering a portion of the filamentary structure such that the bone graft particles do not coat the covered portion of the filamentary structure during the scaffold mixture applying step.

24. The method of claim 21, further comprising any one or any combination of vibrating, translating and rotating a container containing the bone graft particles and the filamentary structure to wedge the bone graft particles between the fibers of the filamentary structure after the scaffold mixture applying step.

25. A method of forming a bioactive filamentary structure, comprising the steps of:
applying synthetic bone graft particles around a filamentary structure;
after the synthetic bone graft particles applying step, applying a polymer solution around the filamentary structure;
after the polymer solution applying step, precipitating a polymer from the polymer solution such that the synthetic bone graft particles and the polymer coat the filamentary structure,
wherein the precipitating step includes the steps of applying a first buffer to the polymer solution after the polymer solution is applied around the filamentary structure to at least partially neutralize the polymer solution and immersing the polymer solution in a precipitating agent after applying both the synthetic bone graft particles and the polymer solution around the filamentary structure, and
wherein the bone graft particles are wedged between fibers of the filamentary structure after the synthetic bone graft particles applying step.

26. The method of claim 25, further comprising any one or any combination of vibrating, translating, and rotating a container containing the bone graft particles and the filamentary structure to wedge the bone graft particles between the fibers of the filamentary structure after the synthetic bone graft particles applying step.

* * * * *